(12) United States Patent
Freeman

(10) Patent No.: US 10,426,664 B2
(45) Date of Patent: Oct. 1, 2019

(54) EYEWEAR WITH VENTILATION OPENINGS

(71) Applicant: Dan W. Freeman, Pleasanton, CA (US)

(72) Inventor: Dan W. Freeman, Pleasanton, CA (US)

( * ) Notice: Subject to any disclaimer, the term of this patent is extended or adjusted under 35 U.S.C. 154(b) by 0 days.

(21) Appl. No.: 16/137,364

(22) Filed: Sep. 20, 2018

(65) Prior Publication Data

US 2019/0117463 A1 Apr. 25, 2019

Related U.S. Application Data

(60) Provisional application No. 62/562,035, filed on Sep. 22, 2017.

(51) Int. Cl.
| | | |
|---|---|---|
| G02C 11/08 | (2006.01) | |
| A61F 9/02 | (2006.01) | |
| G02C 11/00 | (2006.01) | |

(52) U.S. Cl.
CPC ............. *A61F 9/028* (2013.01); *A61F 9/025* (2013.01); *G02C 11/08* (2013.01); *G02C 11/12* (2013.01)

(58) Field of Classification Search
CPC ....................................................... G02C 11/08
USPC ................................................. 351/62; 2/435
See application file for complete search history.

(56) References Cited

U.S. PATENT DOCUMENTS

| | | |
|---|---|---|
| 1,936,746 A | 11/1933 | Baker |
| 1,996,587 A | 4/1935 | Meyrowitz |
| 3,015,987 A | 1/1962 | Harrison |
| 3,160,735 A | 12/1964 | Aufricht |
| 3,517,393 A | 6/1970 | Beauchef |
| 3,663,959 A | 5/1972 | Loubeyre |
| 4,317,240 A | 3/1982 | Angerman et al. |
| 4,785,481 A | 11/1988 | Palmer, III et al. |
| 4,877,320 A | 10/1989 | Holden |
| 4,934,807 A | 6/1990 | Bollzé et al. |
| 4,977,627 A | 12/1990 | Metcalfe et al. |
| 5,239,320 A | 8/1993 | Allendorf et al. |
| 5,300,963 A | 4/1994 | Tanaka |
| 5,339,119 A | 8/1994 | Gardner |
| 5,363,512 A | 11/1994 | Grabos, Jr. et al. |
| 5,423,092 A | 6/1995 | Kawai |
| 5,542,130 A | 8/1996 | Grabos, Jr. et al. |
| 5,610,668 A | 3/1997 | Mage |

(Continued)

FOREIGN PATENT DOCUMENTS

| | | |
|---|---|---|
| AU | 2013308734 B2 | 7/2016 |
| CN | 205007112 | 2/2016 |

(Continued)

OTHER PUBLICATIONS

Search Report and Written Opinion of the International Searching Authority for International Application PCT/US2018/052285, application part, Jan. 8, 2019, 14 pages plus cover, European Patent Office, NL.

*Primary Examiner* — Hung X Dang
(74) *Attorney, Agent, or Firm* — James R. Cypher; Charles R. Cypher

(57) ABSTRACT

Eyewear is provided that has one or more lenses and a shield, the shield comprising a material that resists the passage of solids and liquids there through, and the shield is formed with one or more adjustable sections that allow one or more vents to be formed in said shield.

20 Claims, 16 Drawing Sheets

(56) References Cited

U.S. PATENT DOCUMENTS

| | | |
|---|---|---|
| 5,652,965 A | 8/1997 | Crooks |
| 5,793,463 A | 8/1998 | Hirschman et al. |
| 5,802,622 A | 9/1998 | Baharad et al. |
| 5,815,235 A | 9/1998 | Runckel |
| 5,898,468 A | 4/1999 | Mage |
| 5,929,963 A | 7/1999 | McNeal |
| 6,050,684 A | 4/2000 | Mage |
| 6,233,342 B1 | 5/2001 | Fernandez |
| 6,282,727 B1 | 9/2001 | Lindahl |
| 6,481,845 B1 | 11/2002 | Gazzara |
| 6,641,263 B2 | 11/2003 | Olney |
| 6,692,124 B2 | 2/2004 | Katz et al. |
| 6,718,561 B2 | 4/2004 | Dondero |
| 6,749,299 B1 | 6/2004 | Hsu |
| 6,793,336 B2 | 9/2004 | Min |
| 6,817,709 B2 | 11/2004 | Min |
| 6,938,277 B2 | 9/2005 | Lindahl |
| 6,969,171 B2 | 11/2005 | Lane et al. |
| 7,036,927 B2 | 5/2006 | Kopfer |
| 7,039,959 B2 | 5/2006 | Dondero |
| 7,200,875 B2 | 4/2007 | Dondero |
| 7,481,529 B1 | 1/2009 | Chen |
| 7,594,280 B2 | 9/2009 | Lindahl |
| 7,743,432 B2 | 6/2010 | Curci |
| 8,028,350 B2 | 10/2011 | Hogen |
| D689,116 S | 9/2013 | Chen |
| 8,938,819 B2 | 1/2015 | McNeal |
| 9,009,874 B2 | 4/2015 | McNeal |
| 9,192,520 B2 | 11/2015 | Cater et al. |
| 9,463,117 B2 | 10/2016 | Belbey et al. |
| 9,956,117 B2 | 5/2018 | Didier |
| 2005/0268385 A1 | 12/2005 | Hartman et al. |
| 2009/0079931 A1 | 3/2009 | Yang |
| 2009/0165184 A1 | 7/2009 | Hogen |
| 2010/0228689 A1 | 9/2010 | Hall |
| 2014/0059747 A1 | 3/2014 | Belbey et al. |
| 2014/0063438 A1* | 3/2014 | Cater ................ A61F 9/028 351/62 |

FOREIGN PATENT DOCUMENTS

| | | |
|---|---|---|
| EP | 1810648 A1 | 7/2007 |
| FR | 776139 A | 7/1934 |
| FR | 1467742 A | 2/1966 |
| FR | 2644706 A1 | 9/1990 |
| GB | 364970 A | 1/1932 |
| WO | WO 2004/098471 A2 | 11/2004 |
| WO | WO 2014/036274 A2 | 3/2014 |

* cited by examiner

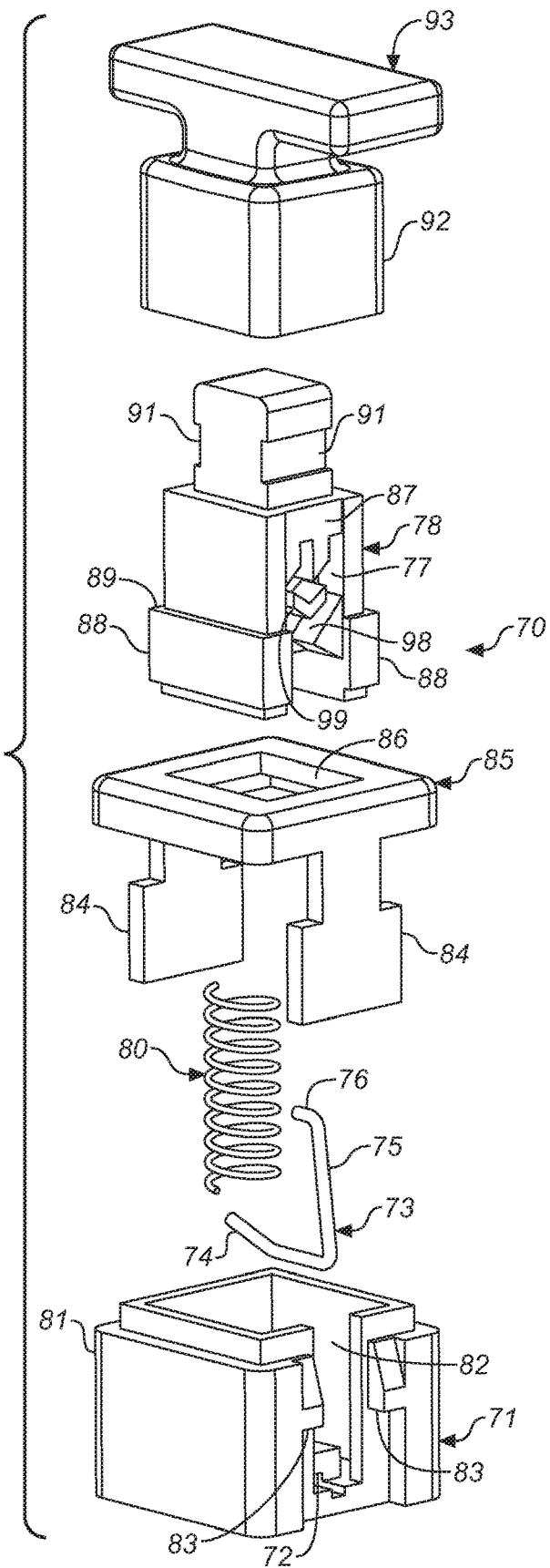

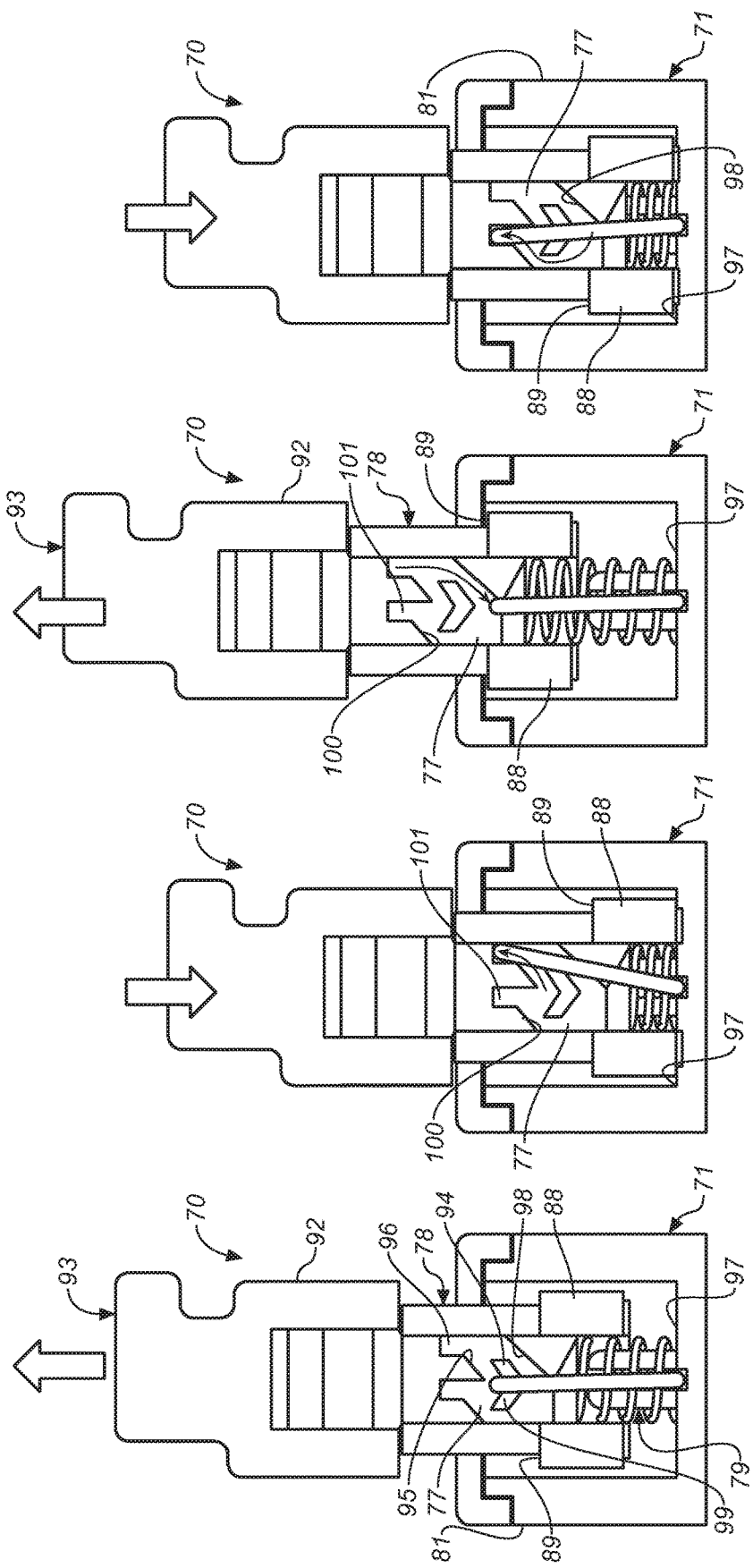

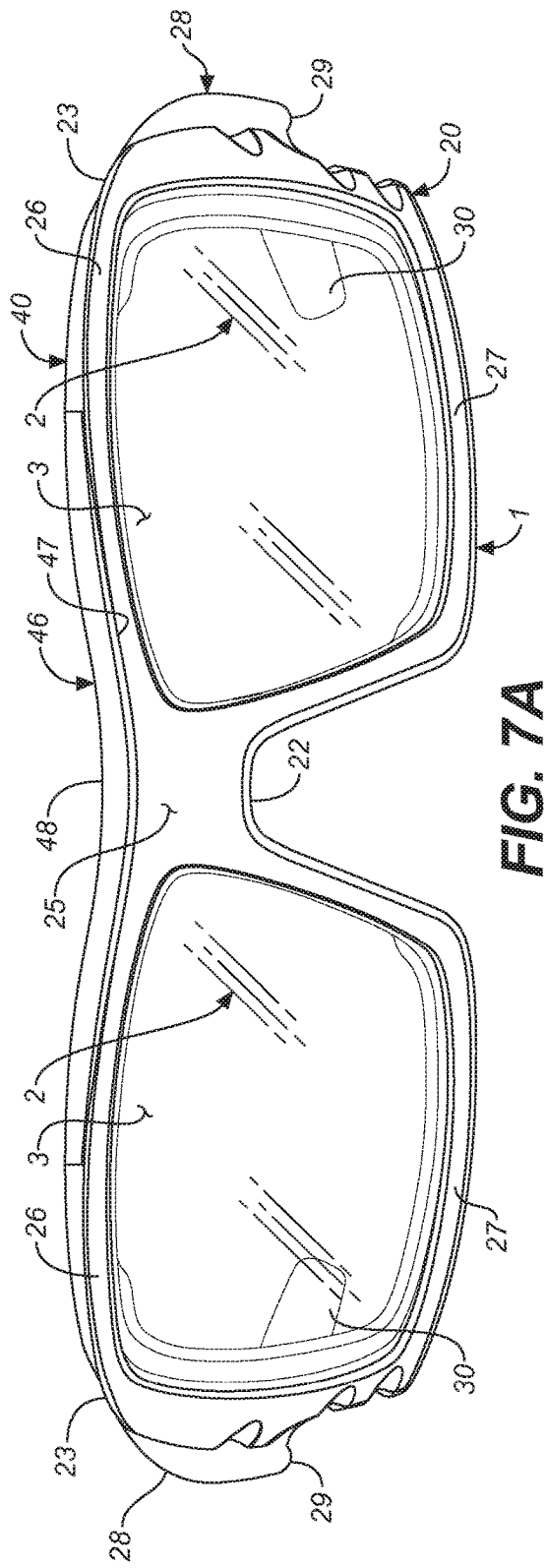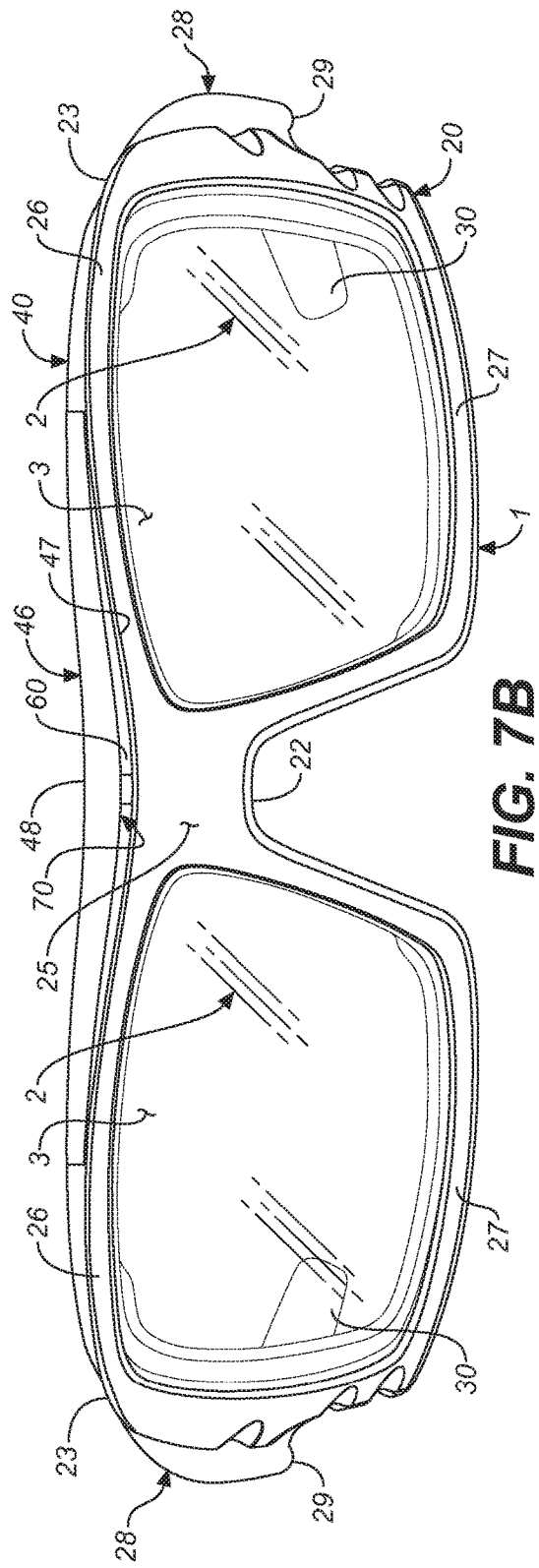

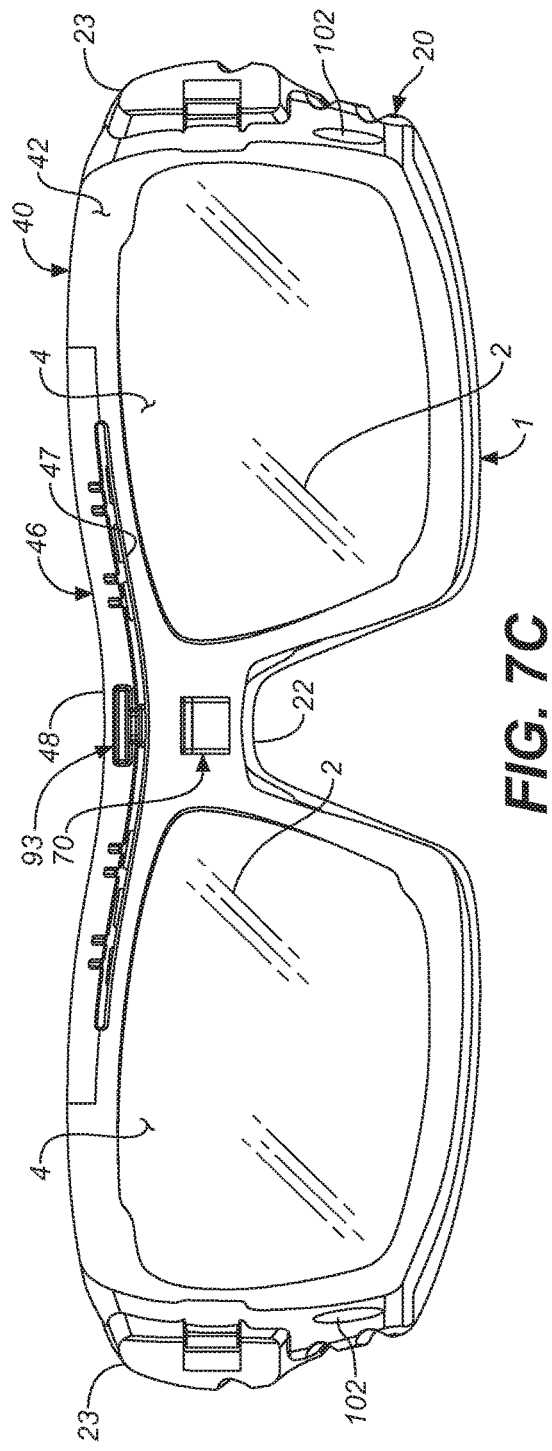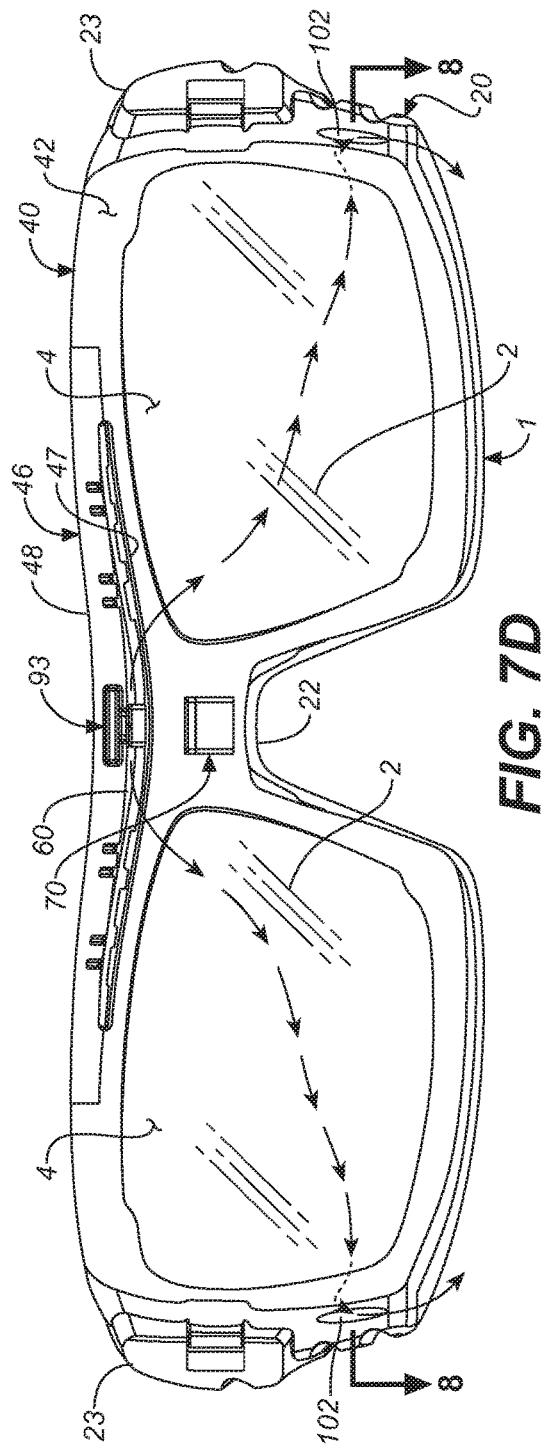

EYEWEAR WITH VENTILATION OPENINGS

BACKGROUND OF THE INVENTION

This invention relates generally to eyewear, and, in particular, to eyewear having a shield at the periphery of the eyewear to help resist the entry of liquids, solids and air into the eyes of the wearer. The shield of the present invention has adjustable components to increase or decrease the amount of ventilation provided to the rearward surfaces of the lenses.

Eyewear to protect a user's eyes from such hazards as glare, radiation, particular matter and moisture and excessive wind can take many forms. Eyewear is used in athletic activities, such as motorcycling, biking, skiing, and running to protect enthusiast's eyes from sprayed liquids and particulate matter entering their eyes as well as to protect their eyes from excessive wind. Eyewear, often known as safety glasses, is also used as protection in hazardous work environments.

Eyeglasses typically include one or more lenses and use temples and a nose piece to support the eyeglasses on the wearer's face. Traditional glasses generally had two lenses, one for each eye. Modern eyeglasses may only have one lens, sometimes called a shield lens. Goggles typically use a nose piece and a band that can be tightened to hold the goggles on the wearer's face. Goggles like eyeglasses can be made with two separate lenses or one lens. Goggles are typically used with a shield around the periphery of the lens to protect the user's eyes. It is well known to add shields around the periphery of eye glasses to increase the protection of the user's eyes. The shield preferably provides a snug fit or seal with both the face of the wearer and with the eyewear. However, the shield can also provide only partial protection to the wearer. The shield could be attached to just the top of the eyewear or to just the sides of the eyewear. The material of the shield can be resilient and can mold itself to the contours of the face to create the seal to help prevent entry of foreign matter into the protected area. The shield helps to protect the eyes from splashed liquids or flying solids as well as wind. While shields increase the protective capabilities of the eyewear, they also increase the possibility that moisture will be trapped between the wearer's face and the lens or lenses of the eyewear that will condense on the one or more lenses and obscure the user's vision.

One solution to this problem is to make the shield air permeable. Permitting air to pass through the shield helps inhibit fogging of the eyewear, but it may not be viable to make the shield material sufficiently air permeable to prevent fogging of the lens or lenses when used by the wearer in a particular situation.

It is an object of the present invention to provide eyewear having an adjustable shield which the user can selectively operate to increase or decrease air flow into the cavity or area between the eyewear and the user's face.

SUMMARY OF THE INVENTION

The present invention provides eyewear having an adjustable shield. The adjustable shield can have an adjustable section that separates or moves away from the remainder or a portion of the shield creating a vent in the shield that allows air to more easily enter behind the lens or lenses of the eyewear.

An object of the present invention is to provide eyewear with a shield that can be releasably attached to the eyewear, yet when it is attached to the eyewear it can also be deformed or split or partially separated from the eyewear to create an opening through which more air can more easily enter behind the lens or lenses of the eyewear.

The shield can be made of air permeable material.

An object of the present invention is to provide a clasp mechanism that allows the user to easily open and close the adjustable section of the shield.

An object of the present invention is to provide eyewear with one or more lenses and a shield where the shield is made of a material that resists the passage of solids and liquids there through. The shield can have forward and rearward surfaces with the forward surface being engaged with the rearward side of the eyewear and the rearward surface of the shield being formed for engaging a wearer's face. The shield can surround the entire periphery of the eyewear or only portions of the eyewear. The forward surface of the shield can have only portions that engage the rearward surface of the eyewear. The rearward surface of the shield can have only portions that engage the face of the wearer. The shield can have at least one lens opening formed therein, the at least one lens opening being positioned about the at least one lens of the eyewear so that the wearer can see through the lens. The shield is positioned with respect to the eyewear so that the wearer can see through the lens or lenses. The shield need not be a continuous member around the lens. The shield is formed with one or more adjustable sections that allow one or more vents to be formed in the shield or between the shield and the eyewear or between the shield and the users face such that air can more easily enter between the lens and face of the wearer.

In one form of the invention, the one or more adjustable sections of the shield are provided at an upper portion of the frame above the one or more lenses.

In one form of the invention, the one or more adjustable sections of the shield are formed with a movable portion and a fixed portion and the vent is formed by moving the movable portion away from the fixed portion.

In one form of the invention, the clasp can hold the movable portion away from the fixed portion.

In one form of the invention, the shield is formed with one or more exit vents. The exit vents can be formed in lower lateral sections of the shield.

In one form of the invention, an attachment portion of the shield releasably engages an attachment portion of the eyewear to connect the shield to the eyewear. The attachment portion of the shield can be located on the forward surface of the shield and the attachment portion of the eyewear can be located on the rearward surface of the eyewear.

BRIEF DESCRIPTION OF THE DRAWINGS

FIG. 4 is an exploded view of a clasp used with the eyewear of the present invention.

FIG. 5A is a side elevation view of the clasp of FIG. 4 showing the clasp in the semi-extended position when the adjustable section of the shield would be closed.

FIG. 5B is a side elevation view of the clasp of FIG. 4 showing the clasp in the opening-intermediary, least-extended position when the user is operating the clasp to go from a sealed state to an open state of the shield.

FIG. 5C is a side elevation view of the clasp of FIG. 4 showing the clasp in the most extended position when the shield would be open to let air into the cavity between the eyewear and the user's face.

FIG. 5D is a side elevation view of the clasp of FIG. 4 showing the clasp in the closing-intermediary, least-extended position when the user is operating the clasp to go from an open state to a closed state of the shield.

FIG. 7A is a front view of the eyewear, in particular eyeglasses, showing the shield in a closed position.

FIG. 7B is a front view of eyewear, in particular eyeglasses, showing the shield in an open position. A portion of the clasp is visible in the space between the upper sealing portion of the shield and the lower sealing portion of the shield.

FIG. 7C is a rear view of the eyewear, showing the shield in a closed position.

FIG. 7D is a rear view of eyewear, in particular eyeglasses, showing the shield in an open position. Portions of the clasp are visible and the upper sealing portion of the shield is spaced from the lower sealing portion of the shield. Arrows show the direction of air flow through the vent created by the opening of the seal at the top of the frame and show air leaving the cavity between the face of the wearer and the eyewear at exit vents in the lower portions of the shield.

DETAILED DESCRIPTION OF THE INVENTION

Figure 10:
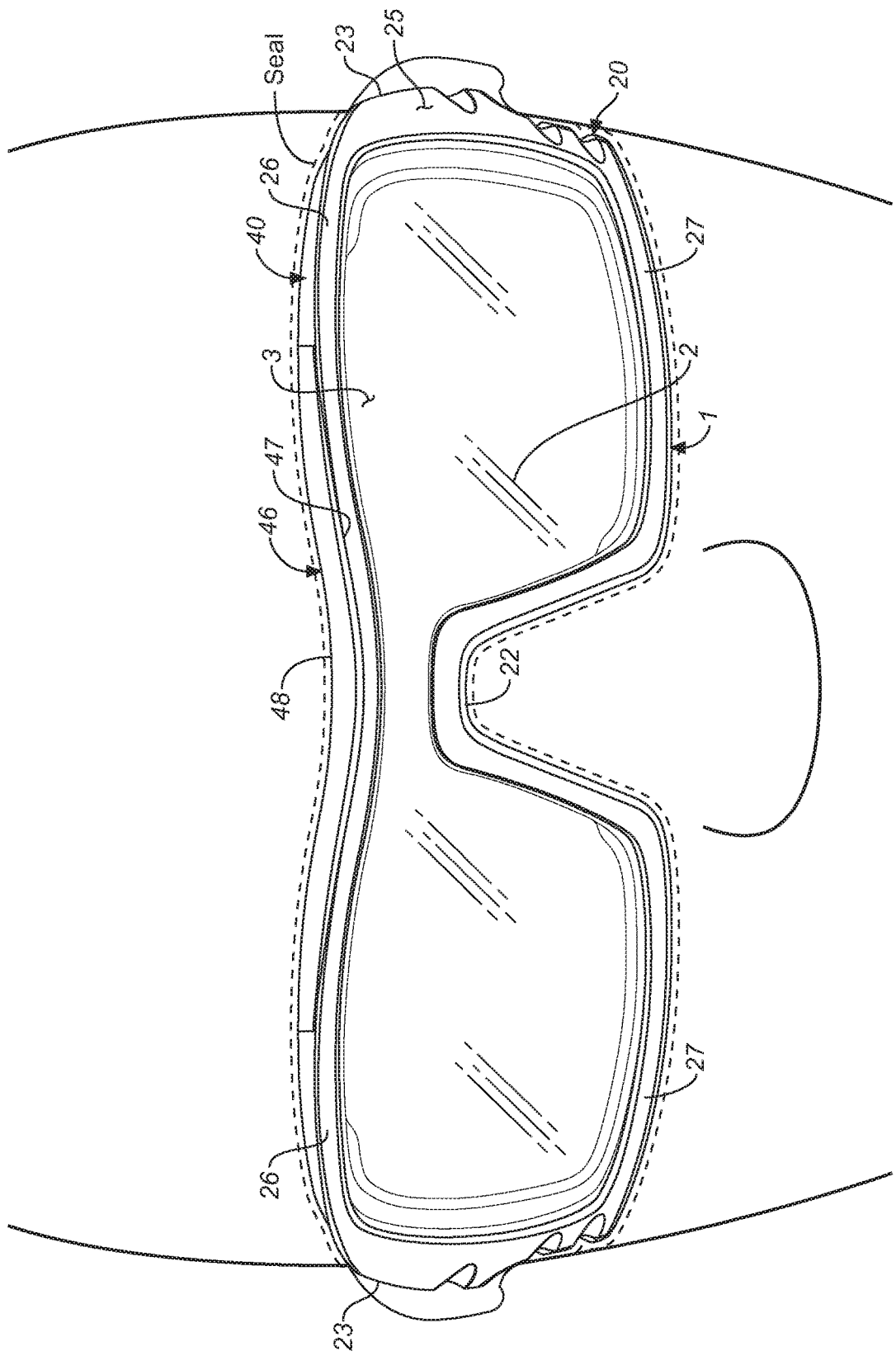
FIG. 10 is a front view of the eyewear of the present invention shown being worn by the user. They eyewear has a single lens as is typical of goggles.

The present invention may be embodied in various forms. The eyewear 1 can be traditional eyeglasses as shown in FIGS. 7A and 7B or traditional goggles as shown in FIG. 10.

Certain directional terms used herein refer to orientation with respect to the wearer. Thus, the terms outward, outwardly, forward, and forwardly, as used herein, refer to a surface or direction facing away from, or a direction extending away from, the face of a wearer of eyewear 1. The terms inward, inwardly, rear, and rearwardly refer to a surface facing toward, or a direction extending toward, the face of the wearer.

Figure 2:
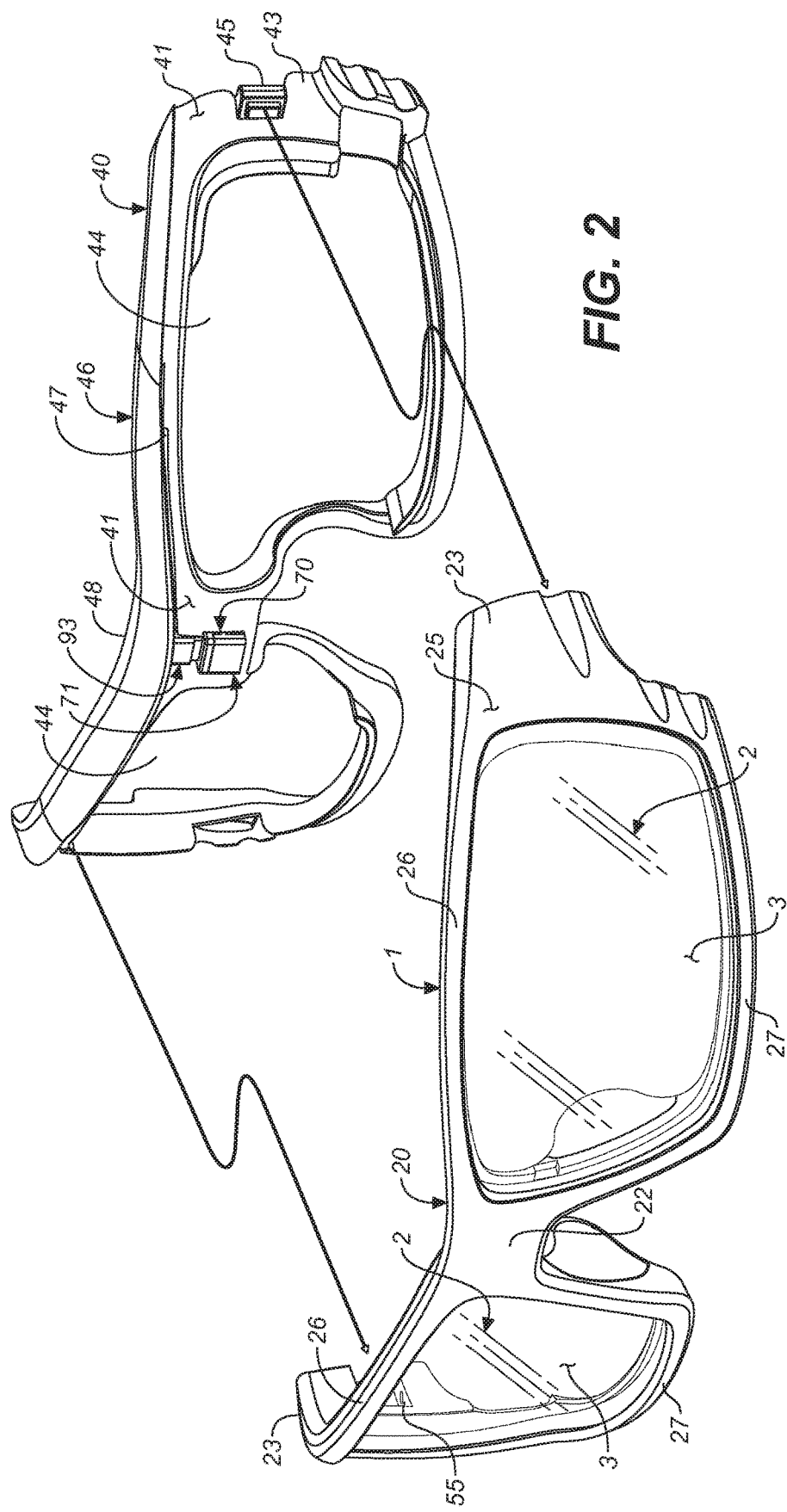
FIG. 2 is a front perspective view of the shield of the present invention and a portion of the frame of the eyewear with the shield removed from the eyewear.
Figure 3:
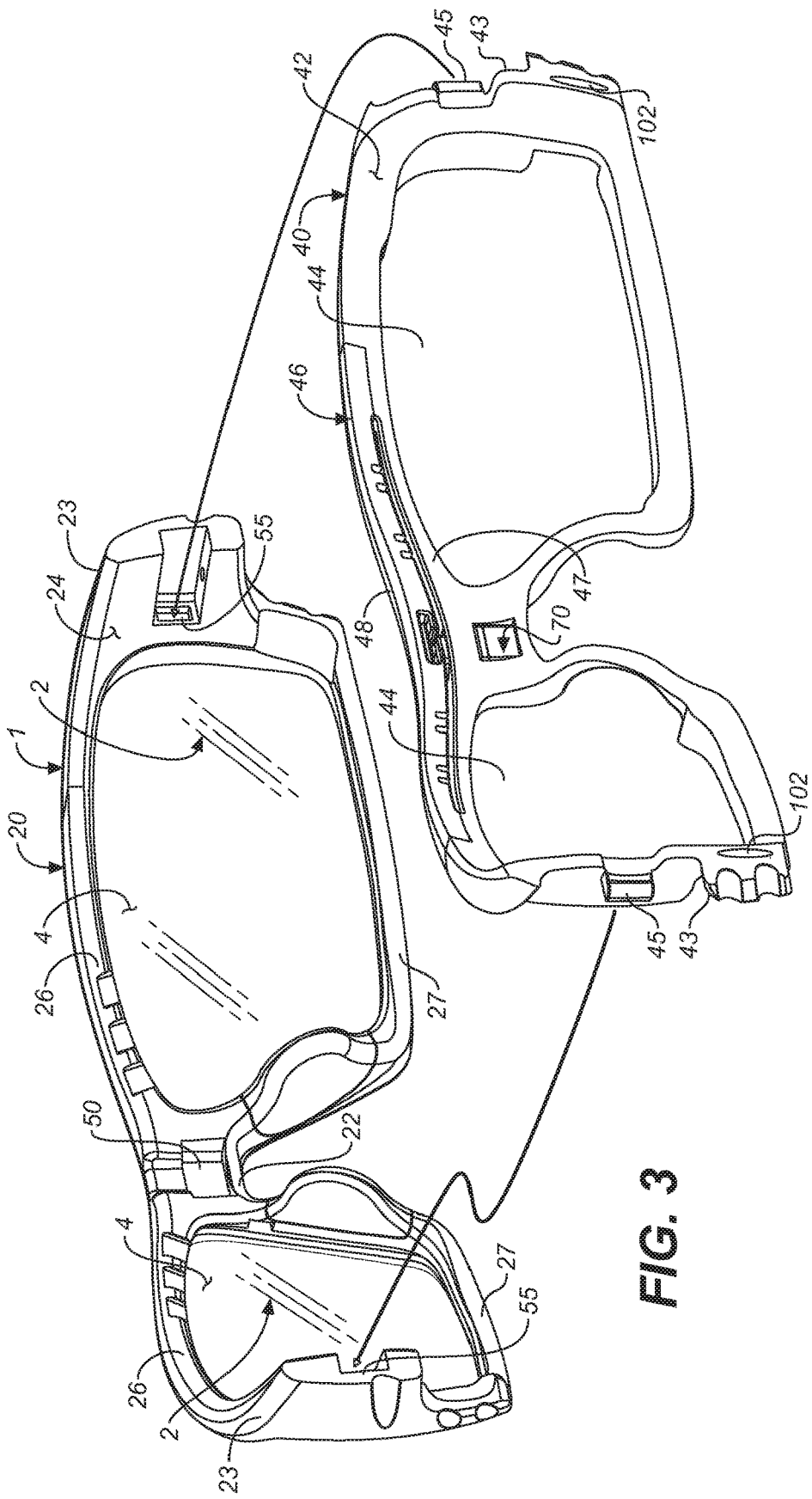
FIG. 3 is a rear perspective view of the shield of the present invention and a portion of the frame of the eyewear with the shield removed from the eyewear.

The eyewear 1 of the present invention includes at least one lens 2 disposed in front of the eyes of the wearer that the wearer looks through. As shown in FIGS. 2 and 3, the eyewear has two transparent lenses 2. As is also shown FIGS. 2 and 3, the lenses 2 have a front surface 3 and a rear surface 4. The eyewear 1 has a front surface and a rear surface, which can be the same surfaces as those of the one or more lens 2, if the eyewear 1 consists of only the one or more lenses 2 without frame members.

As shown in FIGS. 2 and 3, the eyewear 1 of the present invention can also have a frame 20, to which the one or more lenses 2 are secured. The frame 20 preferably has a nose bridge 22 disposed in the center of the frame 20 and frame ends 23 that are laterally disposed from the nose bridge 22 and are disposed at or near the lateral extent of the one or more lenses 2 that the user looks through. The frame has a rearward surface 24 and a forward surface 25.

As shown in FIGS. 7A and 7B, frame 20 includes left and right upper frame pieces 26, and left and right lower frame pieces 27. The frame pieces 26 and 27 can be joined at the center of the frame 20 at the nose bridge 22 and the laterally extending frame pieces 26 and 27 can be joined again at the opposed frame ends 23. As shown in the FIGS. 7A and 7B, the frame members serve to enclose and retain the left and right lenses 2; however the frame 20 does not need to enclose the one or more lenses 2. Further the present invention does not require the use of a frame 20 with the one or more lenses 2. If the eyewear 1 does have a frame 20, all of the above-identified frame members need not be present, including the nose bridge 22 and the opposed frame ends 23. A nose support member could also be directly attached to the lens or lenses 2 of the eyewear 1.

As shown in FIGS. 7A and 7B, the eyewear 1 of the present invention can also include a pair of temple arms 28.

As shown in the figures, the temple arms 28 are connected to the laterally opposed frame ends 23 of the frame 20. The temple arms 28 are shown secured to the frame 20. The temple arms 28 can pivot with respect to the one or more lenses 2 and the frame 20, but they may be fixed with respect to the one or more lenses 2 and the frame 20. As shown, the temple arms 28 can be formed of an extender 29 and an earpiece 30. If no frame 20 is present, the temple arms 28 could be connected directly to the one or more lenses 2. Other methods of supporting the eyewear 1 on the face of the user in front of the eyes of the wearer include using a strap joined to the eyewear 1 that wraps around the head of the user or attaching the eyewear 1 to a helmet or hat worn by the user.

The temple arms 28 and the frame 20 may be formed of any suitable material, including, for example, plastic, or a partially or fully coated core material, such as metal or plastic. In certain embodiments, the temple arms 28 and the frame 20 may be formed of a flexible, resilient material. In other embodiments, the temple arms 28 and frame 20 may be formed of a rigid material. Other suitable materials for the temple arms 28 and frame 20 will be readily apparent to those skilled in the art.

According to the present invention, the eyewear 1 is provided with a shield 40. The shield 40 has a contoured front portion that abuts or is closely adjacent to the frame 20 or to the one or more lenses 2, preferably to create a substantial seal with the eyewear 1, and the shield 40 has a rearward portion that is in contact with at least a portion of the face of the wearer. Portions of the front portion of the shield 40 may also be removed from the frame 20. As shown in the drawings, the shield 40 has a contoured front surface 41 that abuts or is closely adjacent to the rearward surface 24 of the frame 20 or to the rearward surface 4 of the one or more lenses 2, preferably to create a substantial seal with the eyewear 1. As shown in the drawings, the shield 40 has a rearward surface 42 that is in contact with at least a portion of the face of the wearer. Preferably a substantial majority of the rearward surface 42 of the shield 40 is in contact with the face of the wearer to create a substantial seal with the face of the wearer. The shield 40 also has left and right shield ends 43. The shield 40 is preferably designed to resist the passage of liquids, solids and air. The shield periphery can be continuous and the shield 40 can have one or more lens openings 44 formed therein. Generally, the shield 40 substantially conforms to the shape of the frame 20, or if the frame 20 is only a partial frame 20 the shield 40 can substantially conform to the shape of the one or more lenses 2 and the outer peripheral shape of the eyewear 1. The shield 40 can be a single member surrounding both eye sockets, or it can be two separate members each surrounding an eye socket. The shield 40 can be formed from a single material, such as an open or closed cell foam, or it can be formed from differing materials such as a more rigid material where the shield 40 interfaces with portions of the frame 20 and a more resilient material where it interfaces with the face of the wearer and where the shield 40 is designed to move from an open position to a closed position.

The shield 40 preferably provides a snug fit or seal between both the face of the wearer and the eyewear 1. Preferably the portion of the shield 40 in contact with the face is resilient and can mold itself to the contours of the face, creating the seal to help preventing entry of foreign matter into the protected area.

The shield 40 is preferably releasably attached to the frame 20. As shown in FIGS. 2 and 3, engagement or attachment portions 45 at the left and right shield ends 43 of the shield 40 mate with engagement or attachment portions 55 on the left and right frame ends 23 of the frame 20, holding the shield 40 in place. As shown in the figures, the attachment portions 45 are contoured projections that interlockingly fit in contoured notches in the frame 20. The shield 40 can be unclipped from the frame 20 so that the frame 20 can be worn without the shield 40. Other structures for releasably connecting the shield 40 to the frame 20 include pin-hole interfaces where pins located on either the frame 20 or the shield 40 are inserted into holes on the other of the shield 40 or the frame 20. The shield 40 can also be permanently fixed to the frame 20, such as with an adhesive.

The shield 40 is preferably adjustable so that one or more portions of the shield 40 can be changed from a sealed position to an open position. The adjustable shield 40 can have one or more adjustable sections 46 where portions of the shield 40 separate from each other or the shield separates from the eyewear 1 or the face of the wearer creating a vent 60 that allows air to more easily enter around or through the shield to behind the lens or lenses 2 of the eyewear 1.

Figure 1A:
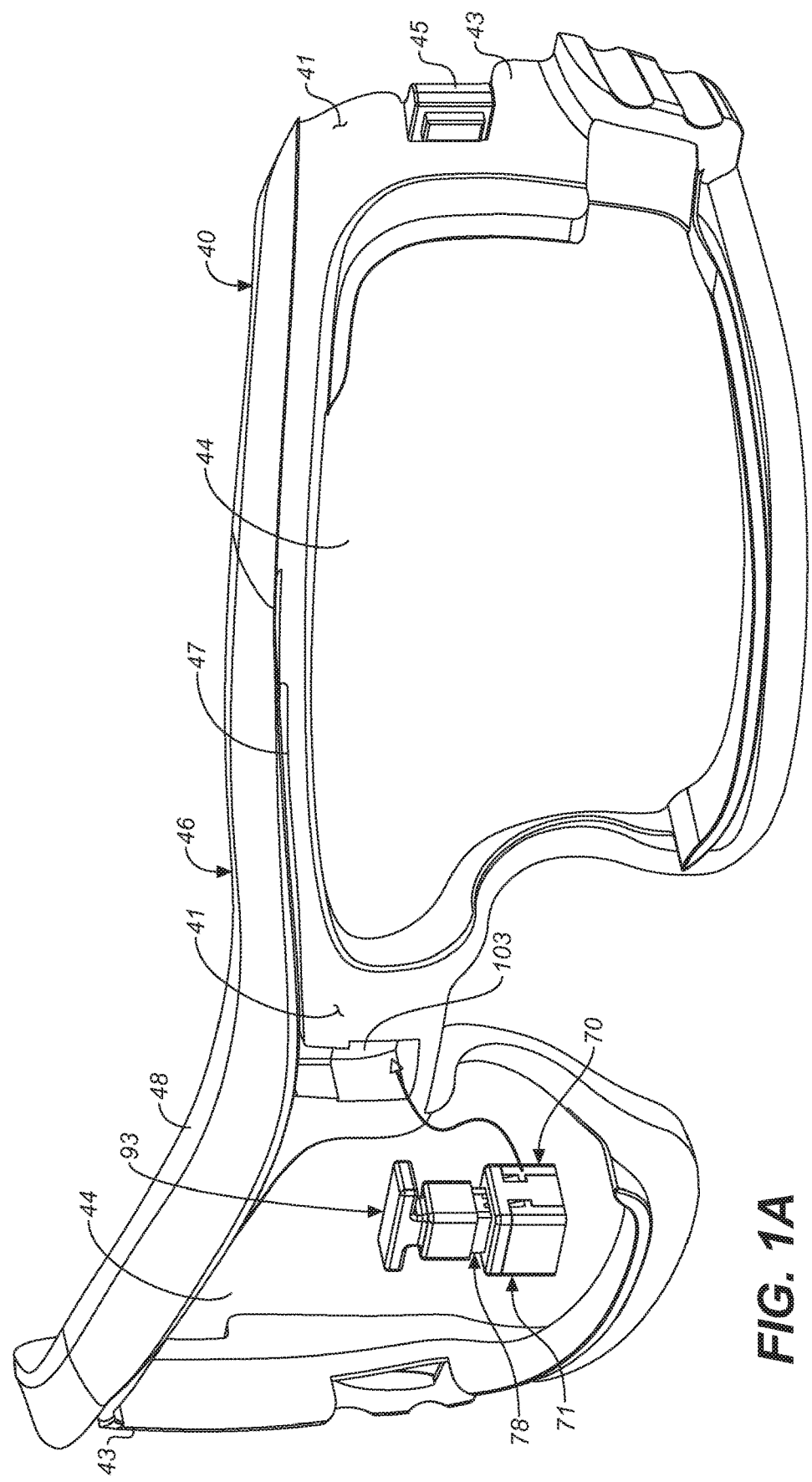
FIG. 1A is a front perspective view of the shield of the present invention and the clasp used with the shield with the clasp removed from the shield.
Figure 1B:
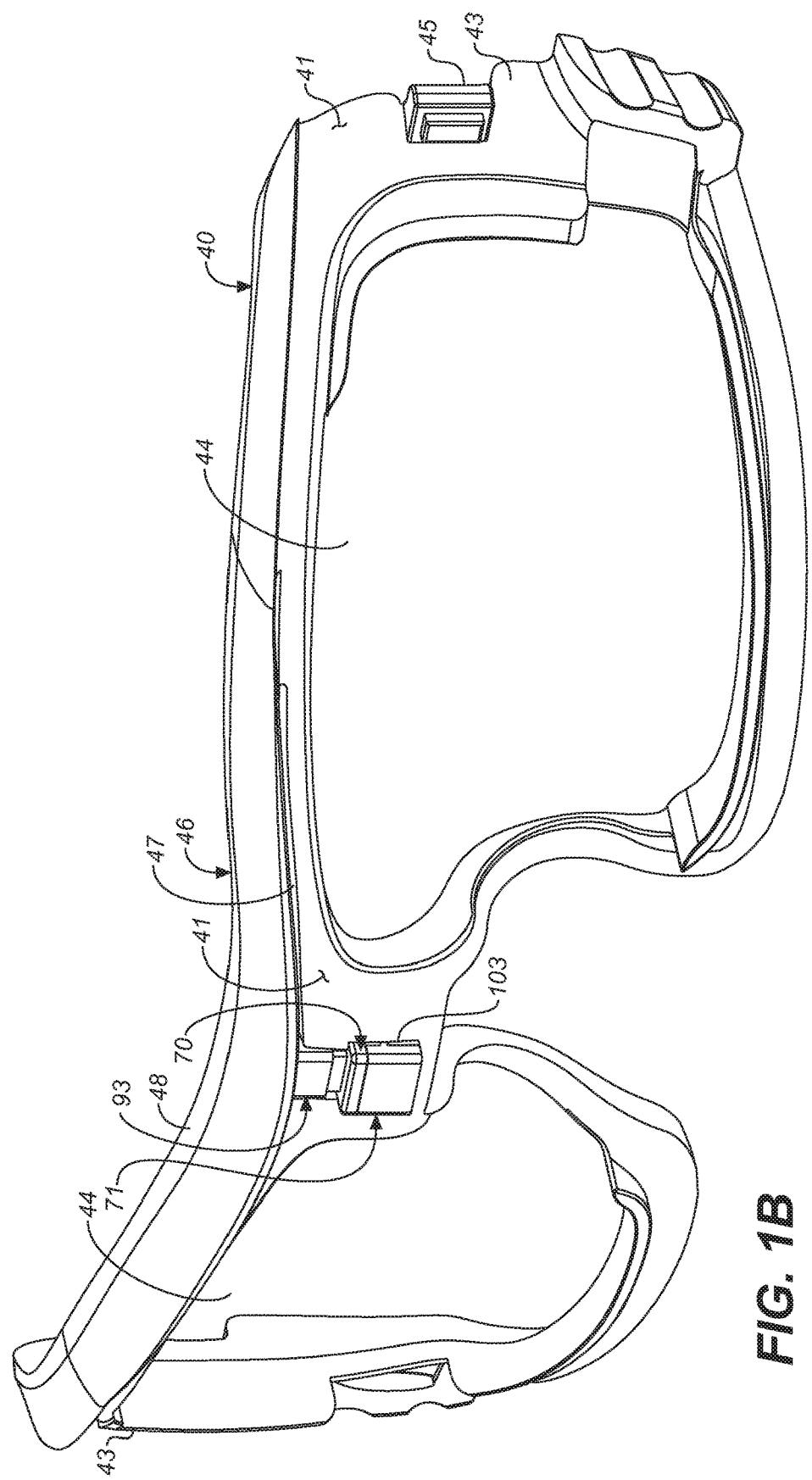
FIG. 1B is a front perspective view of the shield of the present invention and the clasp used with the shield in place.

As shown in FIG. 1A, the shield 40 can be provided with one or more clasps 70 to toggle the one or more adjustable sections 46 of the shield 40 from the open to the closed position. The clasp 70 can be located in a cavity 50 provided in the frame 20 with portions of the clasp 70 protruding from the cavity 50. The clasp is also partially received in a cavity 103 in the shield 40. The clasp 70 works with the adjustable section 46 of the shield 40. As shown in the figures, the clasp 70 is positioned with respect to the frame 20 and extends through a fixed portion 47 of the adjustable section 46 where it is connected to a movable portion 48 of the adjustable section 46.

As shown in FIG. 4, the clasp 70 is made up of a number of components. The clasp 70 is described with an orientation corresponding to that shown in the drawings for clarity, but the clasp could operate if it was disposed at the lateral sides of the eyewear 1 or bottom of the eyewear 1. The clasp base 71 serves as the seat of the clasp 70. The seat of the clasp generally remains in a fixed position with respect to the frame 20 or eyewear 1 and an adjustable portion of the clasp 70 extends or contracts from the seat of the clasp 70, creating an opened or closed position of the clasp 70. The clasp base 71 has a catch 72 which holds the cam follower 73. The cam follower 73 has a hook portion 74 that is received in the catch 72, an extending arm 75 that reaches upwardly, and a flanged end 76 that is received by the cam track 77 in the cam member 78. The clasp base 71 also has a spring retainer or post 79 that receives and positions the spring 80. As shown in FIGS. 5A-5D, the post 79 can lie above the catch 72 that holds the cam follower 73 and is preferably disposed in the center of the clasp base 71. The clasp base 71 is formed with one or more upwardly extending walls 81. As show, the walls 81 can be formed with notches 82 having shoulders 83 that receive and interlock with downwardly extending legs 84 of the clasp cover 85. The clasp cover 85 is formed with an opening or notch 86 that receives the cam member 78. The spring 80 is provided to exert an upward force on the cam member 78. The cam member 78 has an inner portion 87 that is formed with the cam track 77. As shown in the drawings the cam member 78 can be made with two downwardly extending legs 88 that have shoulders 89 that can engage the clasp cover 85 and prevent the cam member 78 from extending upwardly from the clasp base 71 beyond a selected distance.

As shown in FIG. 4, the cam member 78 also has a top extension 79 that is fitted with grooves 91 that can engage the bottom 92 of a catch member 93 that will engage the movable portion 48 of the adjustable section 48 of the shield 40. The catch member 93 has an extending flange 94 that engages the movable portion 48 of the adjustable section 46. The top extension 90 of the cam member could also be formed with a flange or other member to engage and control the position of the movable portion 48 of the adjustable section 46.

FIG. 5A shows a side elevation view of the clasp 70 in the semi-extended position when the adjustable section 46 of the shield 40 would be closed. That is the movable portion 48 would be in close proximity to or engaging the fixed portion 47 to create a better seal. FIG. 5B shows the clasp 70 in the opening-intermediary, least-extended position when the user is operating the clasp 70 to go from a sealed state to an open state of the shield 40. FIG. 5C shows the clasp 70 in the most extended position when the adjustable section 46 of the shield 40 would be open to let air into the cavity between the eyewear 1 and the wearer's face. FIG. 5D shows the clasp 70 in the closing-intermediary, least-extended position when the user is operating the clasp 70 to go from an open state to a closed state of the shield 40.

As shown in FIGS. 5A-5D, the spring 80 places a constant upward load on the cam member 78. The shape of the cam member 78 determines the reciprocating motion of the cam follower 73. The cam member 78 moves upwardly under the force provided by the spring 80 and the user can move the cam member 78 downwardly by imparting force to the top of the cam member 78. In the clasp 70, the elevation of the cam follower 73 is fixed while the cam member 78 moves in relation to the cam follower 73. The motion of the cam follower 73 is constrained by the cam member 78, because the cam follower 73 travels in a cam track 77 formed in the cam member 78. The cam track 77 can be shaped in a manner so that the direction of movement of the cam follower 73 around the cam track 77 is always the same through each cycle and this causes the clasp 70 to reliably toggle from an open to a closed position. As shown in FIGS. 5A-5D, the cam follower 73 moves in a clock-wise manner around the cam track 77.

Figure 6A:
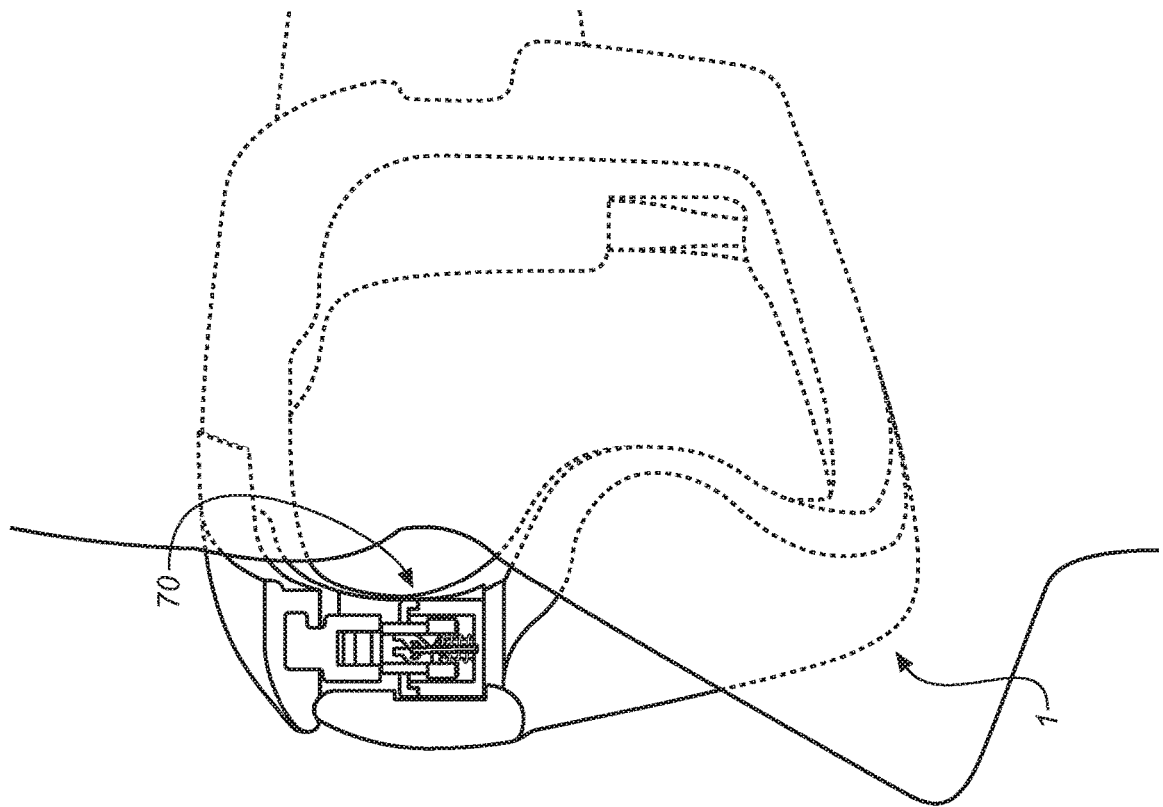
FIG. 6A is a cross-sectional, side view of the eyewear as it would be positioned on a user's face, showing the clasp in the closed position as shown in FIG. 5A and the adjustable section of the shield is closed.
Figure 6B:
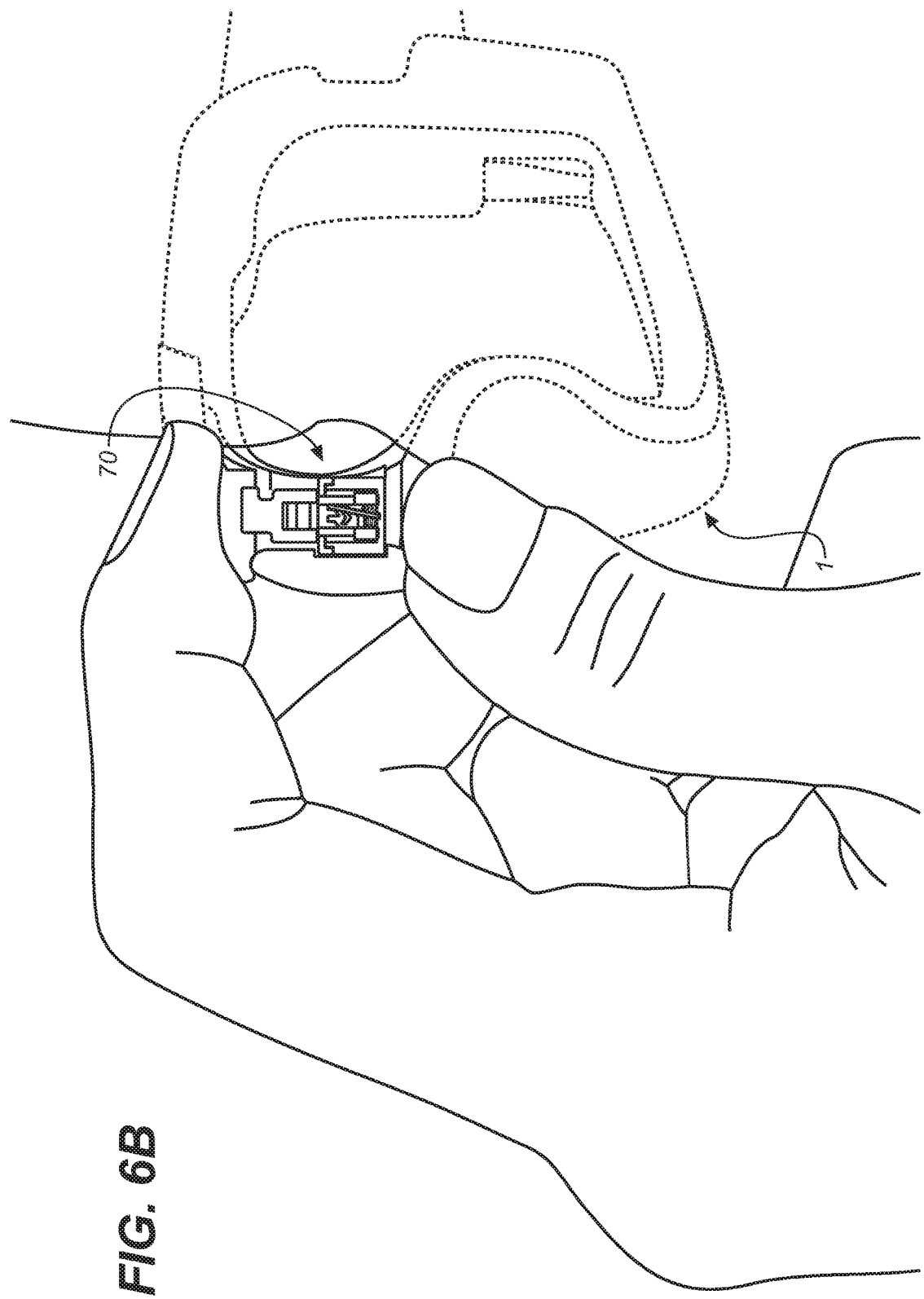
FIG. 6B is a cross-sectional, side view of the eyewear as it would be positioned on a user's face, showing the hand of the user pushing down on the clasp with a finger while resisting that downward force on the clasp with their thumb to move the clasp into the opening-intermediary position shown in FIG. 5B.
Figure 6C:
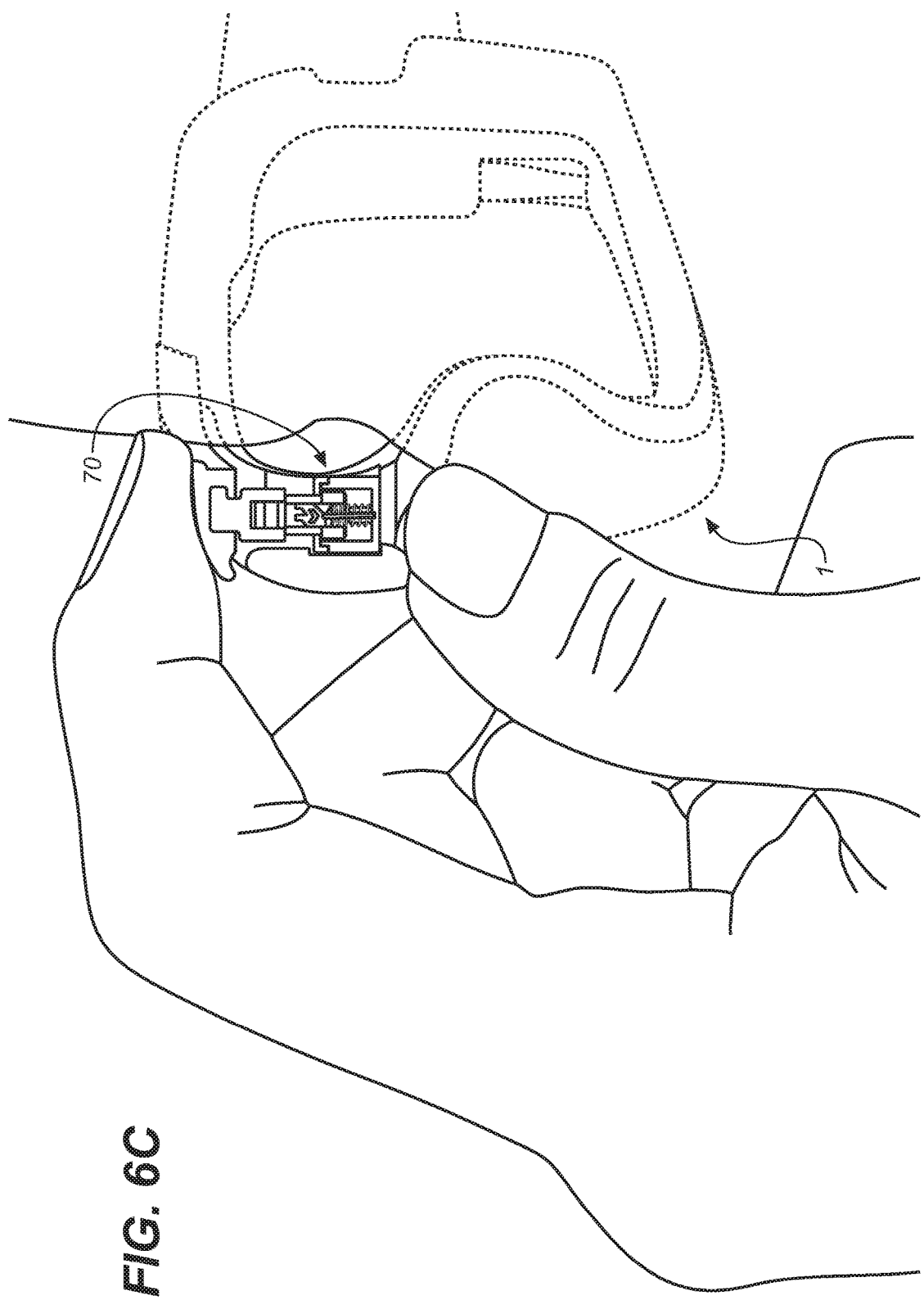
FIG. 6C is a cross-sectional, side view of the eyewear as it would be positioned on a user's face, showing the hand of the user with a finger on the seal and the thumb supporting the clasp from below with the clasp shown in the fully extended position shown in FIG. 5C and the adjustable section of the shield in the open position. With the hand in this position and the clasp in the open position the user could have either just completed releasing the clasp so it could extend to the fully-extended portion or they are about to compress the clasp and close the seal.
Figure 6D:
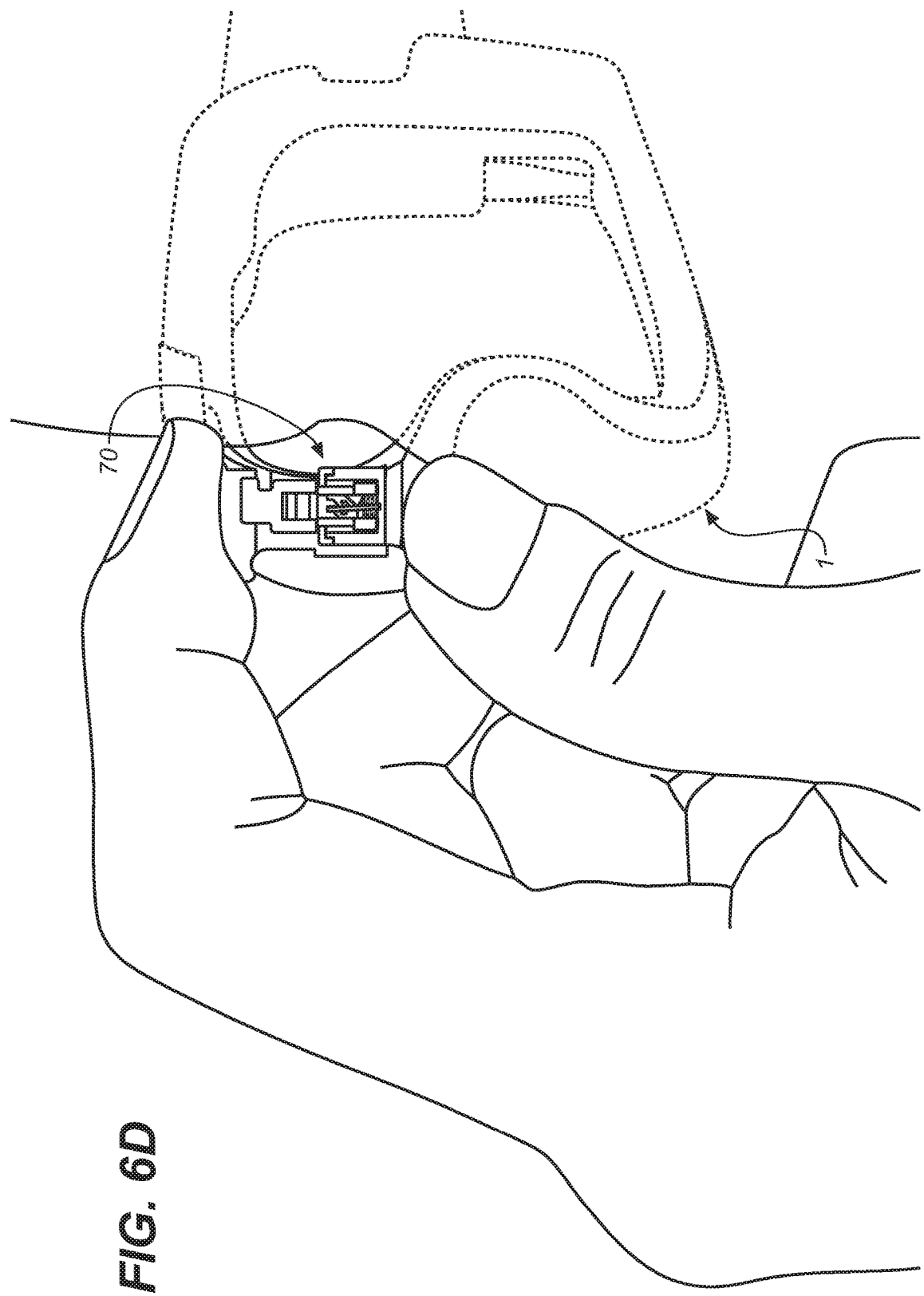
FIG. 6D is a cross-sectional, side view of the eyewear as it would be positioned on a user's face, showing the hand of the user pushing down on the clasp with a finger while resisting that downward force on the clasp with their thumb to move the clasp into the closing-intermediary position shown in FIG. 5D. To complete the closing operation, the user releases the clasp so that there is no downward force on the cam member and the spring in the clasp pushes up on the cam member and the follower catches hold of the return, holding the clasp in intermediary extended position where the adjustable section of the shield would be closed as shown in FIG. 5A.

FIGS. 5A-5D and FIGS. 6A-6D show the elements of the cam track 77. As shown in FIGS. 5A and 6A there is no downward force on the cam member 78 and the spring 80 in the clasp 70 is pushing up on the cam member 78. The cam follower 73 has caught hold of the chevron-shaped return 94, holding the clasp 70 in the intermediary extended position where the adjustable section 46 of the shield 40 would be closed. In FIGS. 5B and 6B a downward force has been exerted on the cam member 78 such that the cam member 78 has moved downwardly with respect to the clasp base 71 and the cam follower 73. As the cam member 78 moves downwardly from the position shown in FIG. 5A, the cam follower 73 engages the central sloped cam surface 95 which directs the cam follower 73 to the right and upwardly into the right lateral slot 96. At this point the legs 88 of the cam member 78 engage the inner bottom surface 97 of the clasp base 70 preventing any further downward movement of the cam member 78. The user then releases the clasp 70 and the spring 80 pushes the cam member 78 upwardly with respect to the cam follower 73. From the position in the right lateral slot 96, the cam follower 73 will ride in the cam track 77 downwardly where the cam follower 73 engages the right lateral sloped surface 98 and moves to a central position. The cam member 78 moves upwardly under the force of the spring 80 until the shoulders 89 on the downwardly extending legs 88 of the cam member 78 engage the clasp cover 85, stopping further upward movement of the cam member 78. This position of the clasp 70 is shown in FIGS. 5C and 6C.

The clasp 70 is now in its most fully extended position and the adjustable section 46 of the shield 40 is open.

To close the adjustable section 46 the user pushes downwardly on the cam member 78. The cam follower 73 will now engage the leftward sloping lower surface 99 of the chevron-shaped return 94 which directs the cam follower 73 to the left where it then engages the left sloping surface 100 of the cam member 78 which directs the cam follower 73 to the right and into the central slot 101 of the cam track 77. This position is shown in FIGS. 5C and 6C. The cam follower 73 is now in a position to re-engage the chevron-shaped return 94 when the user releases the clasp 70 and the spring 80 pushes the cam member 78 upwardly such that the cam follower engages the chevron-shaped return 94 as shown in FIGS. 5A and 6A.

FIGS. 7A and 7B show a front view of eyewear 1, incorporating the present invention. FIG. 7A shows the shield 40 in a closed position with the movable portion 48 of the adjustable section 46 engaging fully or substantially engaging the fixed portion 47 along the entire length or a substantial length of the movable portion 48. FIG. 7B shows the shield 40 in an open position. The upper portion of the clasp 70 is visible in the space between the movable portion 48 of the adjustable section 46 and the fixed portion 47 of the adjustable section 46.

Figure 8:
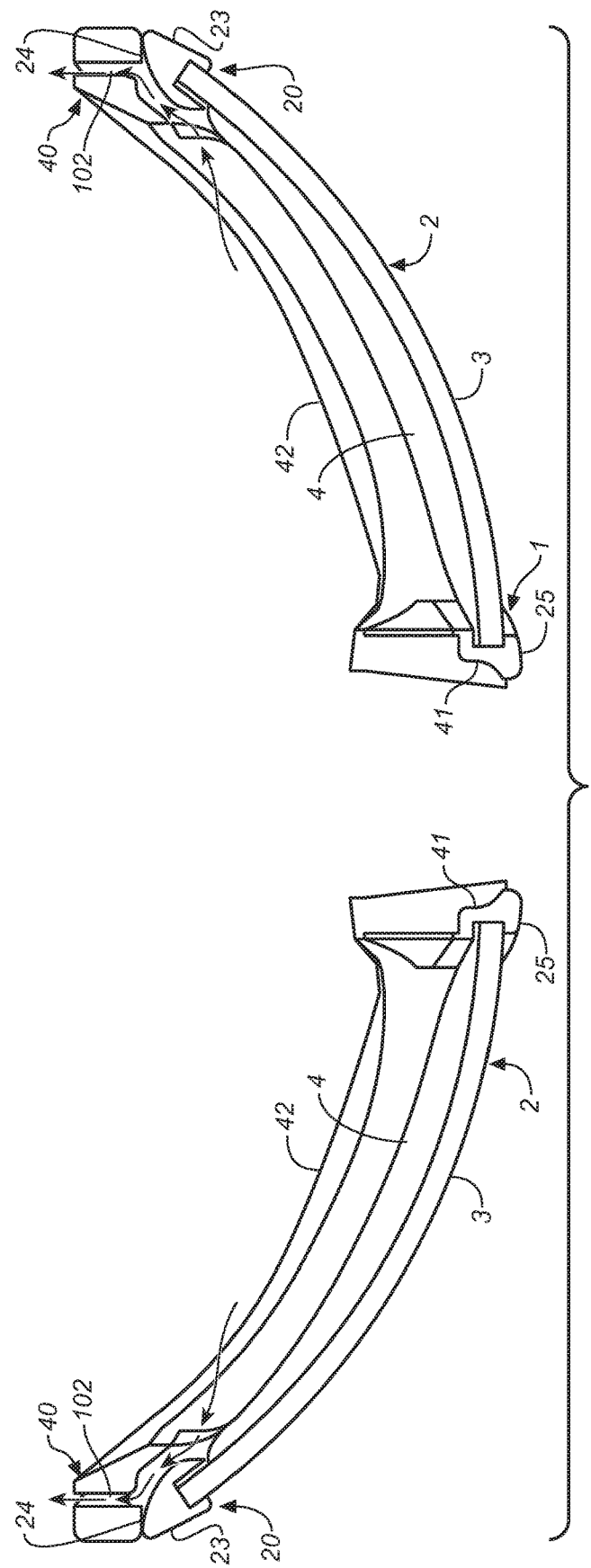
FIG. 8 is cross-sectional top view of the frame and shield of the eyewear, showing air leaving the space behind the lenses and the eyewear through exit vents in the lower portions of the shield.

FIGS. 7C and 7D show a rear view of the eyewear. The temple arms 28 are not shown in FIGS. 7C and 7D. In FIG. 7C, the shield 40 is shown in a closed position. FIG. 7D shows the shield 40 in an open position. Portions of the clasp 70 are visible and the movable portion 48 of the adjustable section 46 is spaced from the fixed portion 47 of the adjustable section 46. Arrows show the direction of air flow through the vent 60 created by the opening of the shield 40 at the top of the frame 20 and show air leaving the cavity between the face of the wearer and the eyewear 1 at exit vents 102 in the lower lateral portions of the shield 40. FIG. 8 shows the air leaving through the lateral lower exit vents 102 in the shield 40. The lateral engagement or attachment members 45 of the shield 40 are shown received in the lateral engagement or attachment members 55 of the frame 20.

FIG. 8 is cross-sectional top view of the frame 20 and shield 40 of the eyewear 1, showing air leaving the space behind the lenses 2 and the eyewear 1 through exit vents 102 in the lower portions of the shield 40.

Figure 9:
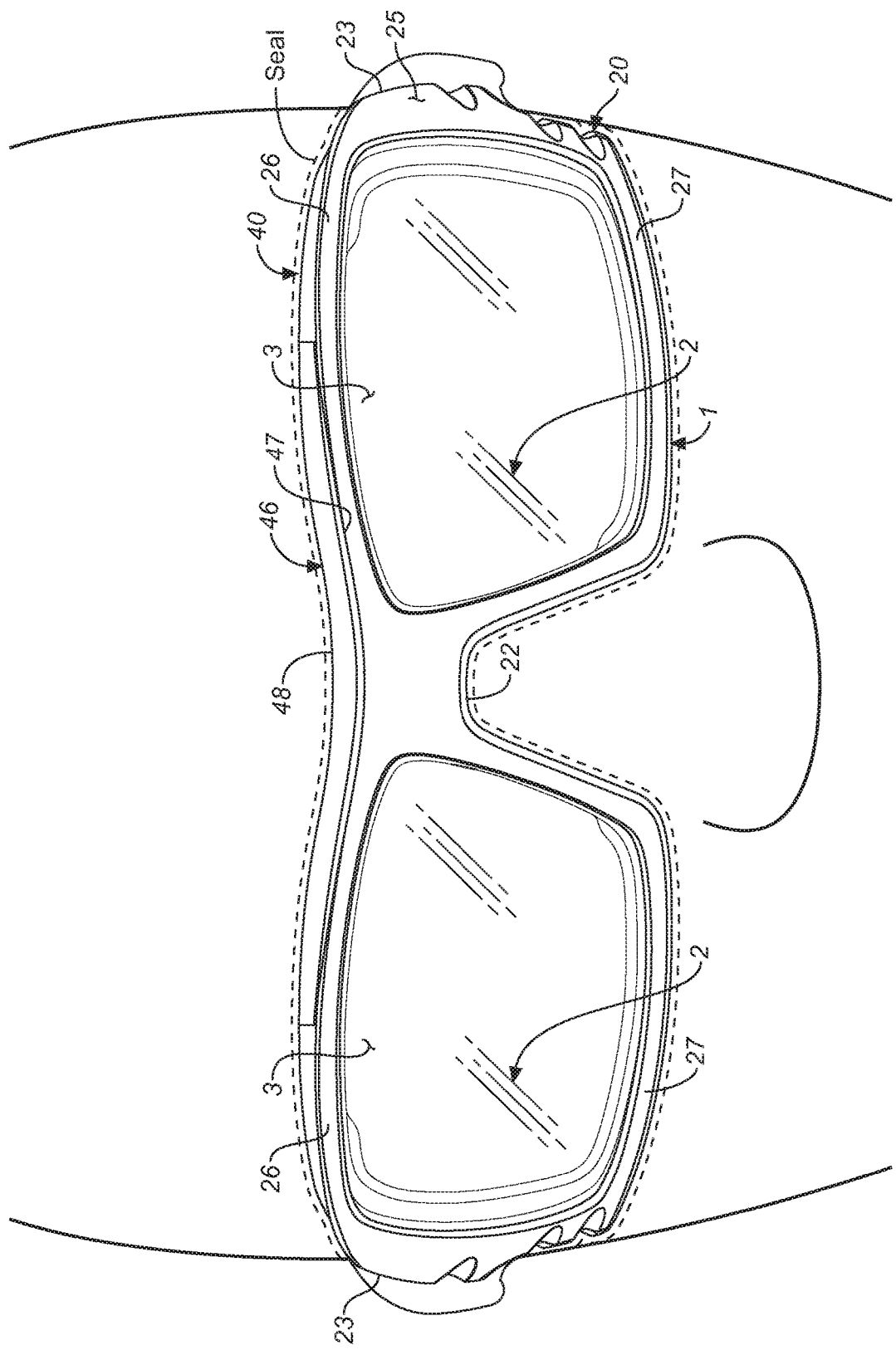
FIG. 9 is a front view of the eyewear of the present invention shown being worn by the user. The eyewear has two lenses as is typical of traditional eyeglasses.

FIG. 9 is a front view of the eyewear 1 of the present invention showing the eyewear 1 being worn by the user. The eyewear 1 has two lenses 2 as is typical of traditional eyeglasses.

FIG. 10 is a front view of the eyewear 1 of the present invention showing the eyewear being worn by the user. The eyewear 1 has a single lens 2 as is typical of goggles.

Figure 11:
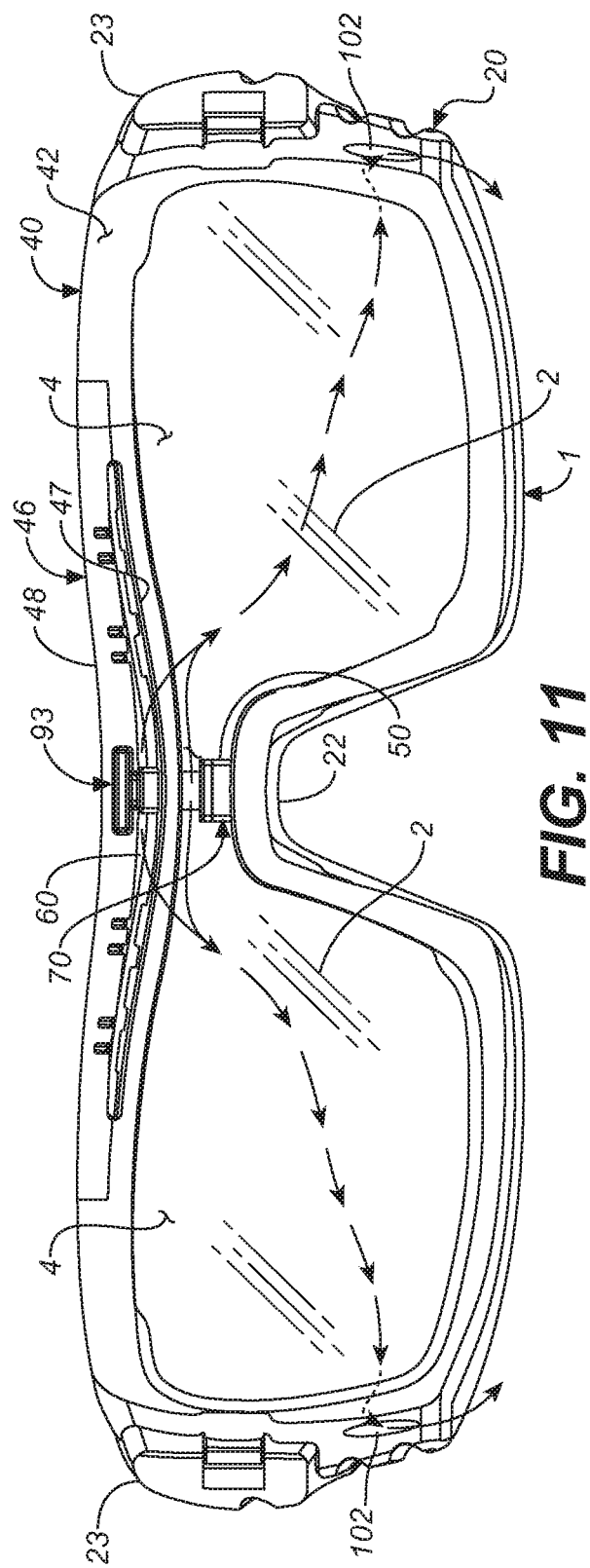
FIG. 11 is a rear view of eyewear, in particular goggles, showing the shield in an open position. Portions of the clasp are visible and the upper sealing portion of the shield is spaced from the lower sealing portion of the shield. Arrows show the direction of air flow through the vent created by the opening of the seal at the top of the frame and show air leaving the cavity between the face of the wearer and the eyewear at exit vents in the lower portions of the shield.

FIG. 11 is a rear view of eyewear 1, in particular goggles, showing the shield 40 in an open position. Portions of the clasp 70 are visible and the upper movable portion 48 of the shield 40 is spaced from the lower fixed portion 47 of the shield 40. Arrows show the direction of air flow through the vent 60 created by the opening of the shield 40 at the top of the frame 1 and also show air leaving the cavity between the face of the wearer and the eyewear 1 at exit vents 102 in the lower portions of the shield 40.

I claim:
1. Eyewear comprising:
a. one or more lenses;
b. a shield, said shield comprising a material that resists the passage of solids and liquids therethrough;

c. said shield having forward and rearward portions, said forward portion engaging said eyewear and said rearward portion of said shield being formed for engaging a portion of a wearer's face, said shield being positioned so that the wearer can see through the lens; and
d. said shield is formed with one or more adjustable sections that allow one or more vents to be formed in said shield such that air can more easily enter between said lens and face of said wearer; wherein
e. the one or more adjustable sections of the shield are provided with one or more clasps for actuating the adjustable sections of the shield between opened and closed positions, the one or more clasps include a spring and a clasp base, the clasp base holds a cam follower and a portion of the cam follower is received by and cycles around a cam track that is part of a cam member with movement of the cam member during the actuating of the adjustable sections of the shield between the opened and closed positions causing movement of the cam follower, the spring biases the cam member away from the clasp base, the cam member has one or more shoulders that engage portions of the clasp and prevent the cam member from extending away from the clasp base beyond a selected distance during the actuating of the adjustable sections of the shield between the opened and closed positions.

2. The eyewear of claim 1, wherein:
the one or more adjustable sections of the shield are provided at an upper portion of the eyewear above the one or more lenses.

3. The eyewear of claim 1, wherein:
the one or more adjustable sections of the shield are formed with a movable portion and a fixed portion and the vent is formed by moving the movable portion away from the fixed portion.

4. The eyewear of claim 1, wherein
said one or more adjustable sections allow the vent to be formed in said shield.

5. The eyewear of claim 1, wherein:
a. the one or more adjustable sections of the shield are formed with a movable portion and a fixed portion and the vent is formed by moving the movable portion away from the fixed portion; and
b. the clasp holds the movable portion away from the fixed portion.

6. The eyewear of claim 5, wherein:
the shield is formed with one or more exit vents.

7. The eyewear of claim 6, wherein:
the exit vents are formed in lower lateral sections of the shield.

8. The eyewear of claim 7, wherein:
an attachment portion of the shield releasably engages an attachment portion of the eyewear to connect the shield to the eyewear.

9. The eyewear of claim 8, wherein:
the attachment portion of the shield is located on the forward surface of the shield and the attachment portion of the eyewear is located on the rearward surface of the eyewear.

10. The invention of claim 9, wherein:
said one or more lenses comprises two lenses, said one or more lens openings in said shield comprises two lens openings, and each of said two lens openings in said shield is positioned about one of said two lenses.

11. The eyewear of claim 10, wherein:
the one or more adjustable sections of the shield are provided at an upper portion of the eyewear above the one or more lenses.

12. The eyewear of claim 8, wherein:
the attachment portion of the shield is located on the forward surface of the shield and the attachment portion of the eyewear is located on the rearward surface of the eyewear.

13. The eyewear of claim 1, wherein:
the shield is formed with one or more exit vents.

14. The eyewear of claim 13, wherein:
the exit vents are formed in lower lateral sections of the shield.

15. The eyewear of claim 1, wherein:
an attachment portion of the shield releasably engages an attachment portion of the eyewear to connect the shield to the eyewear.

16. The invention of claim 1, wherein:
said one or more lenses comprises two lenses, said one or more lens openings in said shield comprises two lens openings, and each of said two lens openings in said shield is positioned about one of said two lenses.

17. The invention of claim 1, wherein:
a. said eyewear is formed with a frame;
b. said clasp is partially received in said frame.

18. The invention of claim 17, wherein:
said clasp is partially received in a cavity in said shield.

19. The invention of claim 1, wherein:
the clasp base remains in a fixed position with respect to the eyewear during the actuating of the adjustable sections of the shield between the opened and closed positions.

20. The invention of claim 1, wherein:
during the actuating of the adjustable sections of the shield between the opened and closed positions causing the movement of the cam follower, the cam track moves both in an upward and downward direction with respect to the cam member and in a left and right direction with respect to the cam member.

* * * * *